(12) United States Patent
Roorda et al.

(10) Patent No.: US 8,517,979 B2
(45) Date of Patent: Aug. 27, 2013

(54) CARRIERS FOR HEMOSTATIC TRACT TREATMENT

(75) Inventors: Wouter E. Roorda, Palo Alto, CA (US); Stefan Richter, Cupertino, CA (US)

(73) Assignee: Abbott Laboratories, Abbott Park, IL (US)

(*) Notice: Subject to any disclaimer, the term of this patent is extended or adjusted under 35 U.S.C. 154(b) by 436 days.

(21) Appl. No.: 12/643,612

(22) Filed: Dec. 21, 2009

(65) Prior Publication Data

US 2010/0228185 A1 Sep. 9, 2010

Related U.S. Application Data

(60) Provisional application No. 61/140,003, filed on Dec. 22, 2008.

(51) Int. Cl.
*A61M 31/00* (2006.01)

(52) U.S. Cl.
USPC .............................. 604/48; 606/139

(58) Field of Classification Search
USPC ................... 604/47, 48, 500; 606/139, 228
See application file for complete search history.

(56) References Cited

U.S. PATENT DOCUMENTS

| | | | |
|---|---|---|---|
| 3,558,771 A | 1/1971 | Balassa | |
| 3,632,754 A | 1/1972 | Balassa | |
| 3,903,268 A | 9/1975 | Balassa | |
| 3,911,116 A | 10/1975 | Balassa | |
| 3,914,413 A | 10/1975 | Balassa | |
| 4,243,656 A | 1/1981 | Walliczek | |
| 4,265,233 A | 5/1981 | Sugitachi et al. | |
| 4,394,373 A | 7/1983 | Malette et al. | |
| 4,474,769 A | 10/1984 | Smith | |
| 4,575,519 A | 3/1986 | Kifune et al. | |
| 4,659,700 A | 4/1987 | Jackson | |
| 4,952,618 A | 8/1990 | Olsen | |
| 4,960,413 A | 10/1990 | Sagar et al. | |
| 5,116,824 A | 5/1992 | Miyata et al. | |
| 5,385,836 A | 1/1995 | Kimura et al. | |
| 5,597,581 A | 1/1997 | Kaessmann et al. | |
| 5,681,334 A * | 10/1997 | Evans et al. | 606/148 |
| 5,738,860 A | 4/1998 | Schonfeldt et al. | |
| 5,836,970 A | 11/1998 | Pandit | |
| 5,951,583 A | 9/1999 | Jensen et al. | |
| 6,007,563 A * | 12/1999 | Nash et al. | 606/213 |
| 6,045,570 A * | 4/2000 | Epstein et al. | 606/214 |

(Continued)

FOREIGN PATENT DOCUMENTS

DE 4337152 5/1995
EP 0319536 3/1992

OTHER PUBLICATIONS

U.S. Appl. No. 61/140,003, filed Dec. 22, 2008, Richter et al.
"Fishery Technology". vol. 11, p. 50, 1974.

(Continued)

*Primary Examiner* — Laura A Bouchelle
*Assistant Examiner* — Gerald Landry, II
(74) *Attorney, Agent, or Firm* — Workman Nydegger; Randy Shen (57) ABSTRACT

Apparatuses and methods for administering a hemostatic agent to the tissue surrounding an opening in a body lumen are disclosed. The apparatus can include a tissue-contacting region and an optional body lumen-penetrating region. At least one hemostatic agent is included as a component of a coating over and/or a mixture with the material of at least a portion of the tissue-contacting region.

16 Claims, 5 Drawing Sheets

(56) References Cited

U.S. PATENT DOCUMENTS

| | | | |
|---|---|---|---|
| 6,126,675 A * | 10/2000 | Shchervinsky et al. | 606/213 |
| 6,350,274 B1 * | 2/2002 | Li | 606/213 |
| 6,719,777 B2 * | 4/2004 | Ginn et al. | 606/213 |
| 7,029,489 B1 * | 4/2006 | Ashby et al. | 606/213 |
| 7,335,220 B2 * | 2/2008 | Khosravi et al. | 606/213 |
| 7,842,068 B2 * | 11/2010 | Ginn | 606/213 |
| 7,918,867 B2 * | 4/2011 | Dana et al. | 606/144 |
| 2002/0038127 A1 * | 3/2002 | Blatter et al. | 606/153 |
| 2003/0120287 A1 * | 6/2003 | Gross et al. | 606/148 |
| 2004/0158287 A1 * | 8/2004 | Cragg et al. | 606/213 |
| 2006/0253037 A1 * | 11/2006 | Ginn et al. | 600/483 |
| 2009/0088609 A1 * | 4/2009 | Schmitz-Rode et al. | 600/301 |

OTHER PUBLICATIONS

"Food Biotechnology", vol. 7, p. 253, 1993.

HemCon Medical Technologies Inc., reprinted—vol. 60, No. 3, 2006.

USA Today, Lifesaving knowldedge, innovation emerge from war's deadly violence, Mar. 27, 2006.

Effect of a Chitosan-Based Hemostatic Dressing on Blook Loss and Survival in a Model of Severe Venous Hemorrhage and Hepatic Injury in Swine, Journal of Trama, vol. 54, No. 1, 2003.

* cited by examiner

CARRIERS FOR HEMOSTATIC TRACT TREATMENT

CROSS-REFERENCE TO RELATED APPLICATIONS

This U.S. Patent Application claims the benefit of and priority to U.S. Provisional Patent Application having Ser. No. 61/140,003, entitled "SHEATHS AS CARRIERS FOR HEMOSTATIC TRACT TREATMENT," and filed on Dec. 22, 2008, the disclosure of which is incorporated herein by reference in its entirety.

FIELD OF THE INVENTION

The present invention relates generally to apparatuses and methods for prevention of bleeding. More particularly, the present invention relates to apparatuses and methods for administering hemostatic agents to tissues surrounding the site of a venous or arterial puncture.

BACKGROUND OF THE INVENTION

A wide variety of sheaths have been developed for use in medical procedures. Sheaths are often used, for example, to access a vessel or artery to allow a surgical procedure to be performed. Sheaths are also used for medical procedures such as angioplasty or stenting that utilize catheters.

In practice, an introducer sheath is generally inserted into the patient's vasculature using the modified Seldinger technique. In the Seldinger technique, a needle is first inserted into the vessel and a guide wire then follows through the needle. Next, the needle is removed and a sheath/dilator combination is advanced over the guide wire. The dilator expands the puncture in the vessel to a size suitable to receive the distal end of an introducer sheath. After the distal end of the sheath is disposed within the vessel, the dilator and guide wire are removed, thereby allowing access to the vessel lumen or other body lumen via the inserted introducer sheath. Thus, the introducer sheath may facilitate introducing various devices into the vessel, while minimizing trauma to the vessel wall and/or minimizing blood loss during a procedure.

Conventionally, introducer sheaths include at least three components: a sheath portion, a hub, and a hemostasis valve disposed within the hub. A suitable example of such an assembly is shown in U.S. Pat. No. 5,807,350, which shows an introducer sheath having a construction similar to that described above, the entirety of which is hereby incorporated by reference.

Upon completion of a procedure, the devices and introducer sheath are typically removed from the patient, leaving a puncture site in the vessel wall. Traditionally, external pressure is applied to the puncture site until clotting and wound sealing occur, however, the patient must remain bedridden for a substantial period of time after clotting to ensure closure of the wound. This procedure, however, may be time consuming and expensive, requiring as much as an hour of a physician's or nurse's time. It is also uncomfortable for the patient, and requires that the patient remain immobilized in the operating room, catheter lab, or holding area.

The time required for clotting is typically increased because patients undergoing catheterization or stenting procedures are generally given systemic anticoagulant drugs to prevent or forestall clot formation. The use of systemic anticoagulants may be medically necessary for many reasons. One important consideration calling for the use of anticoagulants is the risk of embolism (i.e., venous or arterial blockage) if a clot forms at the puncture site and that clot subsequently dislodges and lodges elsewhere in the patient's circulatory system. Regardless of whether the patient is given systemic anticoagulants, there is also a risk of the hematoma formation at or near the puncture site due to bleeding from the tissue around the access site and the opening in the lumen itself. A hematoma at or near the puncture site can cause the patient extreme discomfort and increase recovery time.

As such, various apparatuses and methods have been suggested for percutaneously sealing a vascular puncture by occluding the puncture site. Apparatuses and methods for sealing vascular punctures include, but are not limited to, use of sutures, clips, plugs, and combinations thereof.

For example, U.S. Pat. No. 5,304,184, issued to Hathaway et al. describes percutaneously suturing the puncture site. Alternatively, U.S. Pat. No. 5,674,231, issued to Green et al., discloses a deployable loop that may be advanced through a sheath into a vessel. The loop is intended to resiliently expand to engage the wall of the vessel, thereby closing the puncture. The sheaths disclosed herein can also be used with a vessel closure device, such as those shown in U.S. Pat. No. 6,197,042 and pending U.S. patent application Ser. No. 10/638,115 filed Aug. 8, 2003 entitled "Clip Applier and Methods." In another example, U.S. Pat. Nos. 5,192,302 and 5,222,974, issued to Kensey et al., describe the use of a biodegradable plug that may be delivered through an introducer sheath into a puncture site. Each of the above referenced patents and applications are incorporated herein in their entireties by reference.

BRIEF SUMMARY

Embodiments of apparatuses and methods for prevention of excess bleeding from the tissues surrounding a venous or arterial puncture site are disclosed. In particular, apparatuses and methods for administering one or more hemostatic agents to the tissues surrounding an opening in a bodily lumen so as to prevent bleeding are disclosed. In practice, a number of apparatuses can be inserted into a patient in, for example, a catheterization or stenting procedure and these apparatuses contact the tissues surrounding the puncture site as well as the vascular tissues in the punctured lumen. Preferably, apparatuses can be configured to administer at least one hemostatic agent to the tissues surrounding a venous or arterial puncture site while simultaneously not introducing the hemostatic agent into the punctured vein or artery.

In one embodiment, the present invention can include an apparatus for administering at least one hemostatic agent to a tissue surrounding an opening in a wall of a body lumen. In one embodiment, the apparatus can include an elongate element having an open proximal end, an open distal end, and a lumen extending therebetween. The apparatus, which may be inserted or otherwise positioned through the skin and tissue surrounding an opening in a body lumen, includes a tissue-contacting region and, optionally, a body lumen-penetrating region. The apparatus, as disclosed herein, may include at least one hemostatic agent as a component of a coating over and/or a mixture with a material comprising at least a portion of the tissue-contacting region. As such, the at least one hemostatic agent may be administered to the tissue surrounding an insertion site without delivering the hemostatic agent into the body lumen.

Suitable examples of hemostatic agents according to the present invention include, but are not limited to, aminocaproic acid, prothrombin, thrombin, thromboxane A2, thromboxane B2, endothelins, vasoconstrictors, adrenergic agents, angiotensins, lysine, polylysine, tranexamic acid, N-acetyllysine-methyl ester, bentonite, collagen, cationic polymers, viscosity increasing polymers, anti-fibrinolytic proteins, coagulation catalyzing compounds, coagulation factors, or crosslinkers, derivatives thereof, pharmaceutically acceptable salts thereof, and combinations thereof.

In one embodiment, the apparatus for administering at least one hemostatic agent to a tissue surrounding an opening in a wall of a body lumen may be an introducer sheath configured to allow access to a vessel or an artery during a medical procedure. Because an introducer sheath is typically inserted through a patient's tissue and into an opening of a blood vessel or another body lumen, selectively including a hemostatic agent on the tissue-contacting region and not on the body lumen penetrating region is a reliable means of administering the hemostatic agent to the tissue without introducing it into the blood vessel or other body lumen.

In another embodiment, the apparatus for administering at least one hemostatic agent to a tissue surrounding an opening in a wall of a body lumen may be a closure element delivery device configured to deliver a closure element to the wall of the body lumen. The closure element delivery device includes a tube set capable of contacting the tissue surrounding the opening without introducing it into the blood vessel or other body lumen.

In yet another embodiment, the apparatus for administering at least one hemostatic agent to a tissue surrounding an opening in a wall of a body lumen may be a suture trimmer configured for tightening and trimming a suture applied to the wall of the body lumen. The suture trimmer includes a shaft assembly capable of contacting the tissue surrounding the opening without introducing it into the blood vessel or other body lumen.

In one embodiment, the elongate element may include depth indicia configured to designate the tissue-contacting region and the body lumen-penetrating region. That is, the depth indicia can be used to help a practitioner deliver the at least one hemostatic agent to the tissue surrounding the puncture site while simultaneously avoiding delivery of the hemostatic agent into the patient's vasculature. In one embodiment, the depth indicia may include a first color on the tissue-contacting region and a second color on the body lumen-penetrating region. In yet another embodiment, the depth indicia may include a radiopaque band. For example, a radiopaque band disposed at the distal end of the tissue contacting region and/or at the proximal end of the body-lumen penetrating can be used in conjunction with x-ray fluoroscopy or another x-ray technique to permit visualization of the relative locations of the tissue-contacting region and the body lumen-penetrating region. In yet a further embodiment, the depth indicia may include at least one bleed back lumen positioned distal to the tissue-contacting region so as to prevent insertion of the tissue contacting region into the opening in the body lumen.

In one embodiment, the present invention can include an introducer sheath configured for administration of at least one hemostatic agent to a tissue surrounding an opening in a wall of a body lumen. In one embodiment, the introducer sheath may include a hub portion having a proximal end and a distal end and a lumen extending therebetween, an elongate tubular portion extending from the hub portion, the elongate tubular portion having a proximal end in fluid communication with the hub, a distal end, and a lumen extending therebetween. According to the present invention, the elongate tubular portion includes a body lumen-penetrating region and a tissue-contacting region having at least one hemostatic agent disposed thereon.

In one embodiment, the introducer sheath may further include a flexible valve member disposed in a proximal end of the hub portion. In one embodiment, the flexible valve member includes a plurality of collapsible openings to prevent leaking and that permit the insertion and removal of a medical device.

In one embodiment, the present invention can include a method for administering at least one hemostatic agent to a bodily tissue surrounding an opening formed in a bodily lumen. The method may include steps of (1) providing at least one elongate element having an open proximal end, an open distal end, and a lumen extending therebetween and at least one hemostatic agent disposed on at least one region of the one elongate element, and (2) inserting the elongate element into a tissue surrounding a venous or arterial puncture and deliver the at least one hemostatic agent to the tissue surrounding the a venous or arterial puncture site while substantially not delivering the at least one hemostatic agent to the inside of the vein or artery.

In one aspect, the elongate can include a tissue-contacting region having a first set of indicia that designate a proximal and/or a distal end of the tissue contacting region and a body lumen-penetrating region having a second set of depth indicia that designate a proximal and/or a distal end of the body lumen penetrating region and least one hemostatic agent disposed on the tissue-contacting region with the body lumen-penetrating region being substantially devoid of hemostatic agent.

In one embodiment, the elongate element may include depth indicia configured to designate the tissue-contacting region, wherein the depth indicia are selected from the group consisting of a first color on the tissue-contacting region and a second color on an optional body lumen-penetrating region, at least one radiopaque band, at least a first bleed back lumen positioned distal to the tissue-contacting region, and combinations thereof.

In one embodiment, the method may further include using the depth indicia to insert the elongate element into the tissue surrounding the venous or arterial puncture so as to deliver the at least one hemostatic agent to the tissue surrounding the a venous or arterial puncture site while substantially not delivering the at least one hemostatic agent to the inside of the vein or artery.

Other aspects and features of the present invention will become apparent from consideration of the following description in conjunction with the accompanying drawings.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

I. Introduction and Definitions

Embodiments of apparatuses and methods for prevention of excess bleeding from the tissues surrounding a venous or arterial puncture site are disclosed. In particular, apparatuses and methods for administering one or more hemostatic agents to the tissues surrounding an opening in a bodily lumen so as to prevent bleeding are disclosed. In practice, a number of apparatuses can be inserted into a patient in, for example, a catheterization or stenting procedure and these apparatuses contact the tissues surrounding the puncture site as well as the vascular tissues in the punctured lumen. Preferably, apparatuses can be configured to administer at least one hemostatic agent to the tissues surrounding a venous or arterial puncture site while simultaneously not introducing the hemostatic agent into the punctured vein or artery.

As used herein, the terms "tissue-contacting" or "tissue-contacting region" refer to the portion or portions of a device, such as an introducer sheath, that can contact a patient's non-vascular tissues. That is, a portion of a device is "tissue-contacting" or a "tissue-contacting region" if it only contacts the tissues surrounding a venous or arterial puncture site without being inserted into or contacting the inside of the blood vessel itself.

As used herein, the terms "body lumen-penetrating," "body lumen-penetrating region," "vessel-penetrating" or "vessel-penetrating region" refer to the portion or portions of a device, such as an introducer sheath, that can contact a patient's circulatory system (i.e., vascular tissue) surrounding a puncture site when the device is inserted into the patient. And while the portions of a device that are "body lumen-penetrating" or "vessel-penetrating" or that define a "body lumen-penetrating region" or a "vessel-penetrating region" will typically contact the tissues surrounding a venous or arterial punctures site when it is inserted into a patient, these portions pass through the tissue and enter the body lumen.

II. Apparatuses for Delivery of Hemostatic Agents

Apparatuses of the present invention can be configured to deliver at least one hemostatic agent to a tissue surrounding an opening formed in and/or adjacent to a wall of a blood vessel or another body lumen. The apparatus can take on a number of configurations. Preferably, the apparatus can include at least one elongate, substantially cylindrical element comprising a tissue-contacting region and a body lumen-penetrating region. At least one hemostatic agent can be included as coating on or as a component of a selected portion (e.g., a tissue-contacting region and not a body lumen-penetrating region) of the elongate, substantially cylindrical element such that the hemostatic agent is administered to the tissue around the puncture site and not into the opening in the lumen itself.

In one embodiment, the apparatus is an introducer sheath that is designed to be inserted into a blood vessel or another lumen of a patient. The introducer sheath can maintain the opening into the lumen and may serve as an access site for catheters, guide wires, and the like. Further discussion of introducer sheaths and their configuration can be found in U.S. patent application Ser. No. 11/427,306 entitled "INTRODUCER SHEATH," the disclosure of which is incorporated herein by reference in their entirety.

In order to reduce the risk of bleeding at or near the opening, at least one hemostatic agent may be applied to a selected portion of the apparatus (e.g., a portion that does contact the tissue surrounding a vessel puncture but that does not contact the inside of the blood vessel). Hemostatic agents may be generally classified as substances that help to stop bleeding around a wound and restore normal circulatory flow. Suitable examples of hemostatic agents include, but are not limited to, aminocaproic acid, prothrombin, thrombin, thromboxane A2, thromboxane B2, an endothelin, a vasoconstrictor, an adrenergic agent, an angiotensin, lysine, polylysine, tranexamic acid, N-acetyl-lysine-methyl ester, bentonite, collagen, chitosan, cationic polymers, viscosity increasing polymers, antifibrinolytic proteins, coagulation catalyzing compounds, coagulation factors, or crosslinkers, derivatives thereof, pharmaceutically acceptable salts thereof, and combinations thereof. The use of hemostatic agents may reduce the risk of bleeding at a puncture site because the agents are generally known to possess properties that help to stop bleeding.

For example, aminocaproic acid, lysine, polylysine, N-acetyl-lysine-methyl ester, tranexamic acid, and anti-fibrinolytic proteins are inhibitors of enzymes that breakdown blood clots and they are often used to treat excessive postoperative bleeding. Thrombin, prothrombin (prothrombin is naturally converted to thrombin by enzymes found in blood), coagulation factors, and crosslinkers act directly to form blood clots. Endothelins are an example of a class of proteins that constrict blood vessels. Vasoconstrictors like endothelins can suppress blood loss by restricting blood flow through blood vessels surrounding a puncture site. Adrenergic agents and angiotensins are additional examples of vasoconstrictors. Bentonite, collagen, chitosan, cationic polymers, and viscosity increasing polymers are agglutinating agents that increase the tendency of red blood cells and other blood factors to cling to one another. When applied locally, bentonite, collagen, chitosan, cationic polymers, and viscosity increasing polymers can help stop blood loss and restore hemostasis.

Figure 1A:
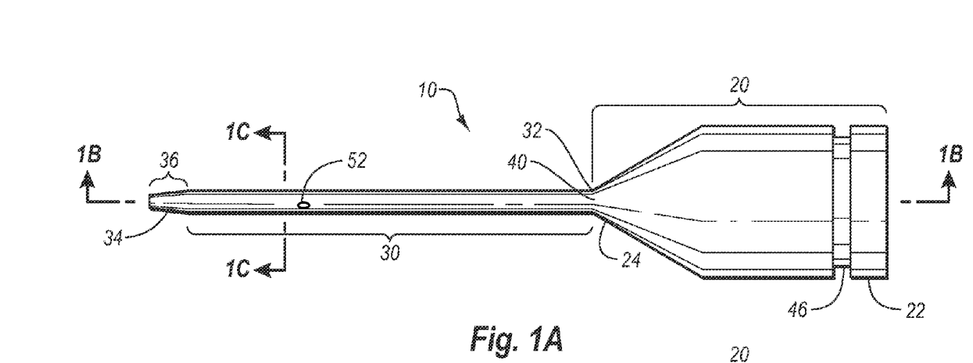
FIG. 1A illustrates a view of an introducer sheath, according to one embodiment of the disclosure.
Figures 1B, 1C:
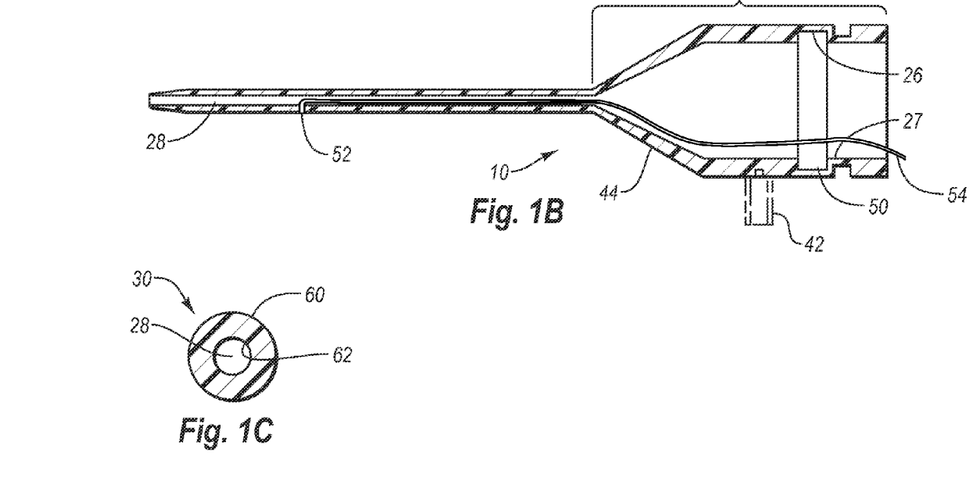
FIG. 1B illustrates a cross-sectional view of the sheath of FIG. 1A taken along the line 1B-1B, according to one embodiment of the disclosure.
FIG. 1C illustrates a cross-sectional view of the sheath of FIG. 1A taken along the line 1C-1C, according to one embodiment of the disclosure.

In one embodiment, the apparatus for administering at least one hemostatic agent to a tissue surrounding an opening in a wall of a body lumen can be an introducer sheath configured to allow access to a vessel or an artery during a medical procedure. With reference to FIGS. 1A-1C, an exemplary embodiment introducer sheath 10 is shown. The introducer sheath 10 can include a hub portion 20 having a proximal end 22 and a distal end 24, and a tubular portion 30 having a proximal end 32 and a distal end 34. The cross section of the hub portion 20 can be generally cylindrical in nature, although other configurations are contemplated. Exemplary configurations or shapes may include, by way of example, oval, polygonal, elliptical, or other cross-section that can be usable for a medical device that is insertable into a body lumen.

The elongate tubular portion 30 extends from the distal end 24 of the hub portion 20. As shown in FIG. 1A, the distal end 34 of the tubular portion 30 can also include a tapered portion 36 that facilitates entry of the introducer sheath 10, for example, into patient's vasculature or other body lumen. The sheath 10 can be formed as a unitary member, or the hub portion 20 and the tubular portion 30 can be formed separately and assembled to form the introducer sheath 10. Because the transition between the hub portion 20 and the tubular portion 30 may introduce a natural flex point, embodiments of the invention can optionally include a strain relief portion 40 which smoothly transitions the tubular portion 30 of the sheath 10 to the hub portion 20. The strain relief portion 40 can be formed at the transition between the hub portion 20 and the tubular portion 30. The strain relief portion 40 can, for example, be configured to provide additional support to at least the proximal end 32 of the elongate tubular portion 30 to prevent kinking at the transition zone of the proximal end 32 of the elongated portion 30 and the distal end 24 of the hub portion 20.

FIG. 1B further illustrates a cross sectional view of the sheath 10 along the line 1B. As shown, a lumen 28 extends from a proximal end 22 of the hub portion 20 to the distal end 34 of the tubular portion 30. The lumen 28 can be generally uniform in cross-section over all or a portion of its length from the proximal end 22 of the hub portion 20 to the distal end 34 of the tubular portion 30. The proximal end 22 of the hub portion 20, within the lumen 28 and defined by the inner wall or surface 52 forming the lumen 28, can also include a feature, such as a receiving feature 26, therein, which is configured to receive a flexible valve member 50. The valve member 50 may be inserted after the sheath 10 is formed. For instance, the receiving feature 26, such as a groove or channel, can receive the valve member 50 and retain the same within the hub portion 20. Optionally, a retaining cap (not shown) disposed adjacent to or within the proximal end of the hub portion 20 can aid the receiving feature 26 to retain the flexible valve member 50 within the hub portion 20. Alternatively, the valve member 50 can be integrally formed with the hub portion 20 during the molding process of the sheath 10 and as such the hub portion 20 need not include the receiving feature 26. The valve member 50 can be configured to be self sealing once it is inserted or formed in the hub portion 20 to prevent fluid escaping from the body lumen.

With continued reference to FIG. 1B, illustrated is an optional port member 42 that may be formed on the outer surface or outer wall 44 of the hub portion 20. The port member 42 may function as a fluid port for the sheath 10. Also formed on the outer surface or wall 44 of the hub portion 20 can be a retention recess or ring 46, as shown in FIG. 1A. The recess or ring 46 may be used to secure a cap (not shown) to the sheath 10. The recess or ring 46 can have various configurations to perform the identified and desired function. For instance, although the walls forming the recess or ring 46 are illustrates as being generally parallel, it will be understood that the recess or ring 46 can have tapered wall, curved wall, combinations of generally parallel, tapered, or curved wall, or generally any other configuration that would allow a cap to be secured thereto or for the recess.

These dimensions of the sheath 10 are often controlled and determined during the manufacturing process. In an injection molding process, for example, the sheath 10 may be formed using a mold. The mold can be machined or configured based on the desired dimensions and configurations of the sheath 10 as described herein. After the mold (which may include more than one part) is formed, the injection molding process can begin by melting a suitable material, such as one described above, and then injecting the melted material into the mold, often under pressure. The mold used in the injection molding process is typically formed such that the molded introducer sheath can be removed after it has cooled and such that the resulting introducer sheath has the desired dimensions and characteristics described herein. As a result, the molded sheath 10 can be a unitary member and may not be assembled from separately formed parts.

Referring now to FIG. 1C, there is shown a cross-sectional view of the sheath 10 in accordance with the present invention along the line 1C-1C of FIG. 1A. The elongate tubular portion 30 can include an outer wall 60 and an inner wall 62 thereby defining a wall thickness. Additionally, the lumen 28 extends along the length of the tubular portion 30.

As mentioned above, although the cross sectional view of the tubular portion 30 is cylindrical in nature, other cross sectional shapes (polygonal, oval, elliptical, rectangular, etc.) are within the scope of the invention. Further, the lumen 28 may also have an alternative cross sectional shape other than circular. In one example, the cross sectional shape of the tubular portion 30 and/or the lumen 28 can be determined by the mold used in an injection molding process. Further, the cross-sectional configuration of the lumen 28 need not be the same as that of the cross-section configuration of the tubular portion 30 as defined by the outer wall of the tubular portion 30, and more generally the sheath 10.

The introducer sheath may be formed, by way of example, using a co-extrusion process or an injection molding process or other method that results in a sheath formed as a unitary member. The process by which an introducer sheath is formed may include the use of one or more materials. The materials can be used simultaneously, or at different stages of the manufacturing process.

Typically, the materials used to form the introducer sheath are medical grade synthetics or plastics. Exemplary materials may include, but are not limited to, flexible PVC, polyurethane, silicone, liner low-density polyethylene ("LLDPE"), polyethylene, high density polyethylene, ("DHPE"), polyethylene-lined ethylvinyl acetate ("PE-EVA"), polypropylene, latex, thermoplastic rubber, and the like. In some embodiments, the materials are configured to have chemical resistance, crack resistance, no toxicity, Food and Drug Administration ("FDA") compliance, non-electrically conductive, dimensional stability, and/or be sterilized by ethylene oxide, gamma radiation, autoclave, UV light, ozone, and the like.

In addition, the selection of materials for a particular sheath can depend on a variety of factors that include, but are not limited to, a particular stiffness and/or flexibility of the sheath or any portion of the sheath, including the desired column stiffness and strength to enable insertion of the sheath, a particular shear or split strength for the sheath or any portion of the sheath, the ability to resist kinking, and the like. For example, the material used for the tubular portion of the introducer sheath may be selected based on shear strength or how easily it can be split. Further, certain features of the sheath may be formed to enhance certain characteristics. For example, a strain relief portion may be formed so as to resist kinking while the elongated tubular portion may be formed to facilitate splitting.

In one embodiment, the sheath 10 illustrated in FIGS. 1A and 1B may include a bleed back lumen 52 and 54 for receiving fluids within the patient contacted by the sheath 10. The bleed back lumen 52 and 54 includes a hole 52 through the wall of the sheath and a tubular member 54 that extends longitudinally from the hole 52 to the proximal end of the sheath. Blood received in the hole 52 and issuing from the tubular member 54 may indicate that the device is located in a blood vessel or other body lumen or cavity intended for treatment. The bleed back lumen 52 and 54 may be disposed near the distal end of the sheath 10 distal to a region coated with a hemostatic agent. In such a case, blood issuing from the tubular member would indicate that the sheath is inserted as far as it can be inserted into the blood vessel without introducing the hemostatic agent into the patient's vasculature.

Figure 2A:
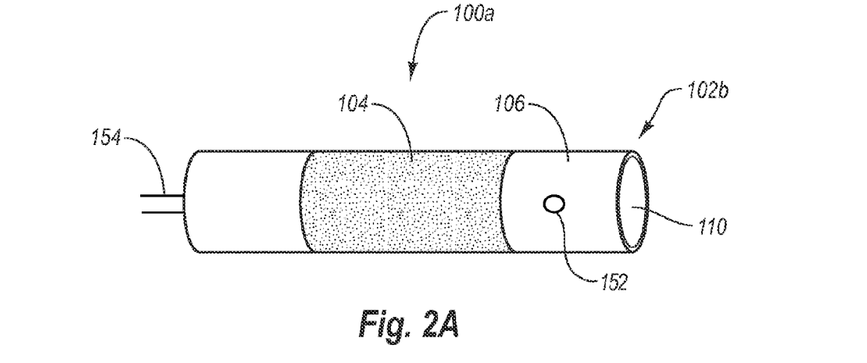
FIG. 2A illustrates a perspective view of a procedural sheath according to one embodiment of the disclosure.
Figure 2B:
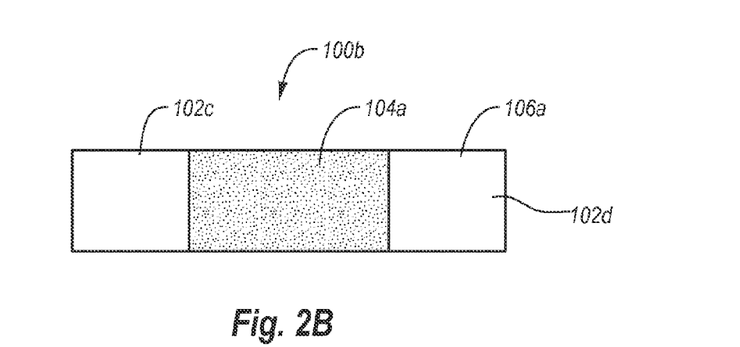
FIG. 2B illustrates another view of the procedural sheath of FIG. 2A, according to one embodiment of the disclosure.
Figure 2C:
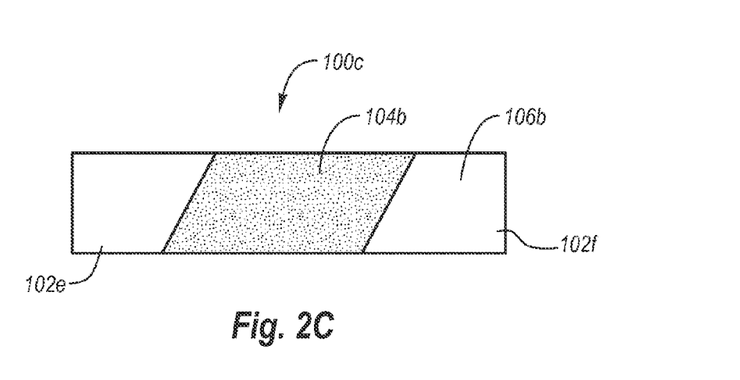
FIG. 2C illustrates an alternative embodiment of a procedural sheath, according to one embodiment of the disclosure.

With reference now to FIGS. 2A-2C, embodiments of introducer sheaths configured for administering at least one hemostatic agent to a tissue surrounding an opening in a wall of a body lumen during a medical procedure are illustrated. An exemplary introducer sheath 100a can have a proximal end region 102a and a distal end region 102b and can include a predetermined length and a predetermined cross-section, both of which can be of any suitable dimension. The sheath 100a also can form a lumen 110 that extends along a longitudinal axis of the sheath 100a and substantially between the proximal and distal end regions 102a, 102b. The lumen 110 can have any suitable internal cross-section and is suitable for slidably receiving one or more devices (not shown), such as a catheter, a guide wire, a closure element applier or the like.

Sheath 100a also includes a tissue-contacting region 104 and a body lumen-penetrating region 106. Because an introducer sheath 100a is typically inserted through a patient's tissue and into an opening of a blood vessel or another body lumen, selectively including a hemostatic agent on the tissue-contacting region 104 and not on the body lumen-penetrating region 106 may be a reliable means of administering the hemostatic agent to the tissue without introducing it into the blood vessel or other body lumen.

Suitable examples of hemostatic agents that can be included as a component of a coating on the tissue-contacting region 104 of the sheath 100a include, but are not limited to, aminocaproic acid, prothrombin, thrombin, thromboxane A2, thromboxane B2, endothelins, vasoconstrictors, adrenergic agents, angiotensins, lysine, polylysine, tranexamic acid, N-acetyl-lysine-methyl ester, bentonite, collagen, chitosan, cationic polymers, viscosity increasing polymers, anti-fibrinolytic proteins, coagulation catalyzing compounds, coagulation factors, or crosslinkers, derivatives thereof, pharmaceutically acceptable salts thereof, and combinations thereof.

The sheath may be formed, by way of example, using a co-extrusion process or an injection molding process or another method known in the art. In one embodiment, the at least one hemostatic agent can be applied to the sheath during the forming process. For example, the at least one hemostatic agent can be applied to one or more cavities of a mold, such as an injection mold, prior to injection of a molten polymer material. In another embodiment, the at least one hemostatic agent can be applied to the sheath after it is formed. For example, the at least one hemostatic agent can be selectively applied to one or more portions of the sheath after forming as part of an overcoat layer.

Selectively applying at least one hemostatic agent to the tissue-contacting region 104 and not to the body lumen-penetrating region 106 of sheath 100a allows a user to administer a hemostatic agent or agents to the tissues surrounding a puncture site without introducing the hemostatic agent into the patient's vasculature. As shown, the body lumen-penetrating region 106 does not include a hemostatic agent. Thus the distal end region 102b, including the body lumen-penetrating region 106, can be substantially devoid of hemostatic material.

The sheath 100a shown in FIG. 2A includes a bleed back lumen 152 and 154 for receiving fluids within the patient contacted by the sheath 100a. As discussed in reference to FIGS. 1A and 1B, blood received in the hole 152 and issuing from the tubular member 514 may indicate that the device is located in a blood vessel or other body lumen or cavity intended for treatment. The bleed back lumen 52 and 54 is disposed near the distal end of the sheath 10 distal to a region coated with a hemostatic agent 104. In such a case, blood issuing from the tubular member would indicate that the sheath is inserted as far as it can be inserted into the blood vessel without introducing the hemostatic agent 104 into the patient's vasculature.

The tissue contacting region can have a number shapes depending on the application. This is further depicted in FIGS. 2B and 2C, which depict differences in shape and extent of the tissue-contacting regions 104a and 104b and the body lumen-penetrating regions 106a and 106b. As shown in FIG. 2B, the margins of the tissue-contacting region 104a and the body lumen-penetrating region 106a are square with the proximal and distal ends 102c and 102d of the introducer sheath 100b. In contrast, FIG. 2C shows tissue-contacting 104b and body lumen-penetrating 106b regions whose margins are angled relative to the proximal and distal ends 102e and 102f of the introducer sheath 100c. The configuration shown in FIG. 2B may be useful if the introducer sheath 100b is to be inserted straight into a patient, whereas the configuration shown in FIG. 2C may be useful if the introducer sheath 100c is to be inserted into a patient at an angle.

In one embodiment, the introducer sheath 100a may include depth indicia configured to designate the tissue-contacting region and the body lumen-penetrating region. That is, the depth indicia can be used to help a practitioner deliver the at least one hemostatic agent to the tissue surrounding the puncture site while simultaneously avoiding delivery of the hemostatic agent into the patient's vasculature.

FIGS. 2A-2C illustrate an embodiment of depth indicia. For example, shaded regions 104-104B can be included on sheath 100a-100c to help a practitioner deliver the at least one hemostatic agent to the tissue surrounding the puncture site while simultaneously avoiding delivery of the hemostatic agent into the patient's vasculature. In an additional embodiment, the depth indicia may include a first color on the tissue-contacting region and a second color on the body lumen-penetrating region. In yet another embodiment, the depth indicia may include a radiopaque band. For example, a radiopaque band disposed at the distal end of the tissue contacting region and/or at the proximal end of the body-lumen penetrating can be used in conjunction with x-ray fluoroscopy or another x-ray technique to permit visualization of the relative locations of the tissue-contacting region and the body lumen-penetrating region.

In one embodiment, medical devices that does not require a sheath and that includes portions that do not contact the patient's vasculature can be used to deliver a hemostatic composition to the tissue surrounding an opening in a body lumen while avoiding delivery of the hemostatic composition to the patient's vasculature.

Figure 3:
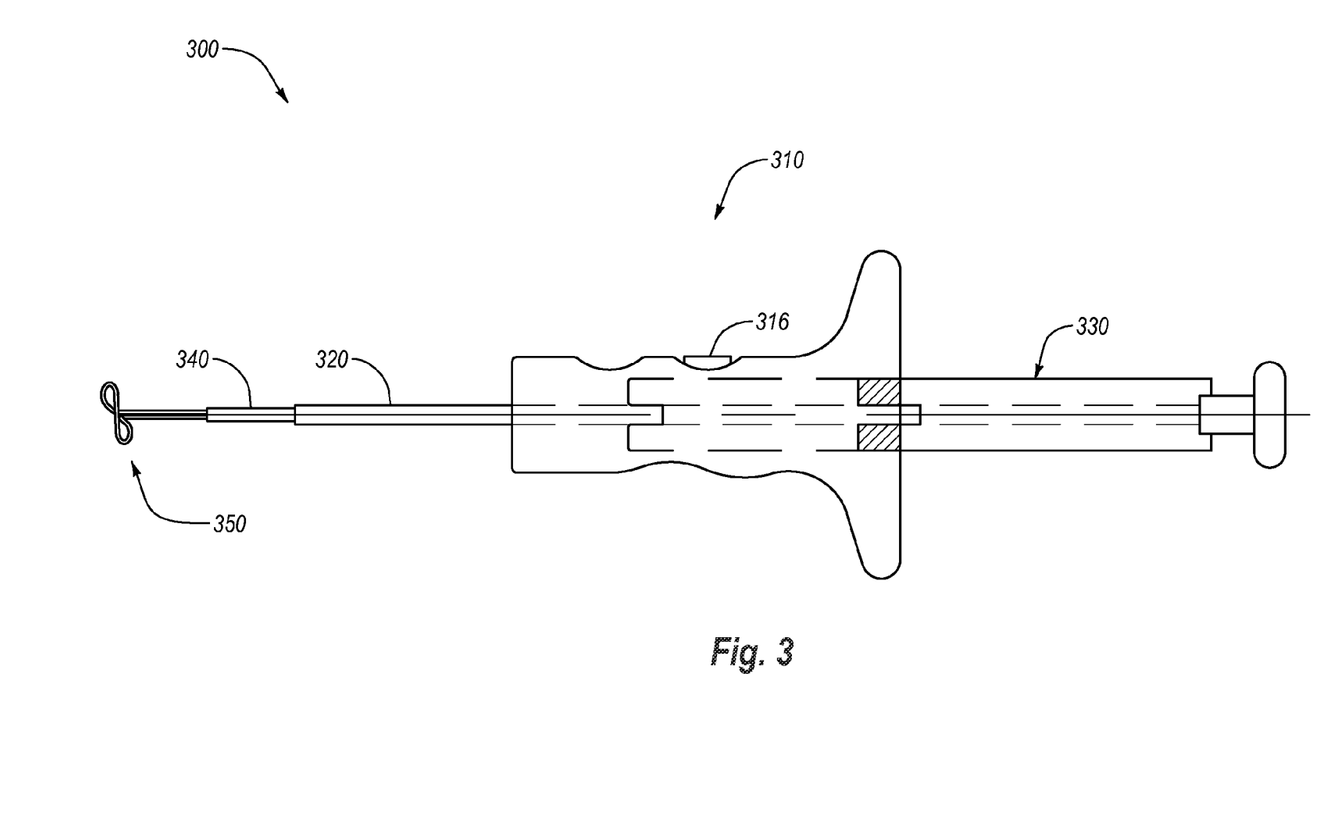
FIG. 3 discloses a closure system in accordance with one example embodiment.

Referring now to FIG. 3, a closure element applier 300 that is illustrated. The closure system 300 may be configured to close an opening in a body lumen. In accordance with the present disclosure, the closure element applier 300 includes a tube set 320 that that may be configured to deliver at least one hemostatic agent to the tissue surrounding an opening in a blood vessel without introducing the at least one hemostatic agent into the blood vessel.

The closure system 300 may include a handle member 310, a tube set 320 coupled to the handle member 310, a plunger member 330, an inner lumen 340, and an anchor member 350 disposed at least partially within the inner lumen 340. An operator, such as a physician, may utilize the closure system 300 and the elements thereof to close an opening in a body lumen. For example, the plunger member 330 may be used to deploy the anchor member 350 to locate the distal surface of a lumen wall and position the closure system 300 relative to a body lumen opening. Thereafter, the handle member 310 and tube set 320 may be used to deliver a closure element, such as a clip or staple, and deploy the closure element into the tissue of the body lumen wall to close or substantially close the body lumen opening.

The handle member 310 may include any number of mechanisms necessary to deploy a closure element. For example, the handle member 310 may include a button 316 operatively associated with one or more mechanisms configured to deploy a closure element. In a further embodiment, the button 316 may be operatively associated with one or more elements of the tube set 320 configured to deploy the closure element 300. As a result, an operator may depress the button 316 in order to push, fire, or eject a closure element from the tube set 320 into the tissue of a body lumen to close a body lumen opening.

The tube set 320 may be configured to contain, deliver, and/or deploy a closure element. In particular, the tube set 320 may include one or more tubular members and/or other mechanisms configured to house, advance, push, fire, and/or eject the closure element. For example, the tube set 320 may include a pusher tube, a garage tube, a carrier tube, and/or other similar elements. In one embodiment, the tube set 320 may include a spring-loaded pusher member configured to deploy the closure element when released or activated.

The closure element may be disposed within the tube set 320 in an initial, open configuration and may be configured to be deployed from the tube set 320 and move to a deployed, closed configuration. In particular, in one embodiment, the closure element may store sufficient energy, while in its initial, open configuration, to engage the tissue of and close an opening in a lumen wall. For example, the closure element may include any of a number of shape memory and/or superelastic materials and may be set to elastically return to a deployed, closed configuration from any other configuration. In one embodiment, the closure element may include nitinol. In a further embodiment, the closure element may be a clip, staple, or other closure element.

Any portion of tube set 320 may include a hemostatic agent as a component of a coating on the tube set 320. Suitable examples of hemostatic agents that can be included as a component of a coating on tube set 320 include, but are not limited to, aminocaproic acid, prothrombin, thrombin, thromboxane A2, thromboxane B2, endothelins, vasoconstrictors, adrenergic agents, angiotensins, lysine, polylysine, tranexamic acid, N-acetyl-lysine-methyl ester, bentonite, collagen, chitosan, cationic polymers, viscosity increasing polymers, anti-fibrinolytic proteins, coagulation catalyzing compounds, coagulation factors, or crosslinkers, derivatives thereof, pharmaceutically acceptable salts thereof, and combinations thereof.

The closure system 300 may also include an inner lumen 340. The inner lumen 340 may be disposed at least partially within the tube set 320, the handle member 310, and/or the plunger member 330. In a further implementation, the inner lumen 340 may be movable, such as slidable, with respect to the tube set 320, the handle member 310, and/or the plunger member 330. As a result, the inner lumen 340 may move either distally or proximally relative to the tube set 320, the handle member 310, and/or the plunger member 330.

The inner lumen 340 may be configured to house and deliver the anchor member 350 to or away from a body lumen opening. In a further embodiment, the inner lumen 340 may be integrated into or replaced by an element of the tube set 320. The inner lumen 340 may include any number of flexible or semi-rigid materials. For example, the inner lumen may include one or more polymers, elastomers, plastics, metals, composites, other similar materials, or combinations thereof.

As introduced above, the closure system 300 may include an anchor member 350. The anchor member 350 may be configured to locate, position the closure system 300 relative to, and/or anchor the tissue surrounding a body lumen opening. The anchor member 350 may be disposed in an initial, contracted configuration within the inner lumen 340. By advancing the plunger member 330 in a distal direction relative to the inner lumen 340, an operator may deploy the anchor member 350 from the distal end of the inner lumen 340. Retracting the plunger member 330 in a proximal direction may position and/or anchor anchor member 350 against a distal surface of a lumen wall. In a further embodiment, further retracting the plunger member 330 in a proximal direction may retract the anchor member 350 from the body lumen and/or into the inner lumen 340 or tube set 320.

In operation, an opening in a vessel may be closed using the closure element applier 300 by at least partially advancing the closure element applier into the tissue surrounding the opening. In particular, the operator may advance the closure element applier 300 until the inner lumen 340 of the closure system 300 extends at least partially into the body lumen. Once the closure system 300 has been advanced at least partially into the body lumen, the operator may deploy the anchor member 350. Once deployed from the inner lumen 340, the anchor member 350 may move from an initial, contracted configuration to a deployed, expanded configuration. The operator may then retract the anchor member 350 to position the anchor member 350 against the distal surface of the lumen wall proximate the body lumen opening. The operator may then deploy the closure element by, for example, pressing button 316. With the closure element in place, the anchor member 350 may be retracted into inner lumen 340 and the closure element applier 300 may be retracted.

Notably, tube set 320 does not contact the inside of the body lumen during the deployment of the closure element. As such, the closure element applier 300 described herein may be used to deliver a hemostatic composition to the tissue surrounding an opening in a body lumen while applying a closure element to the opening in the body lumen.

Figure 4:
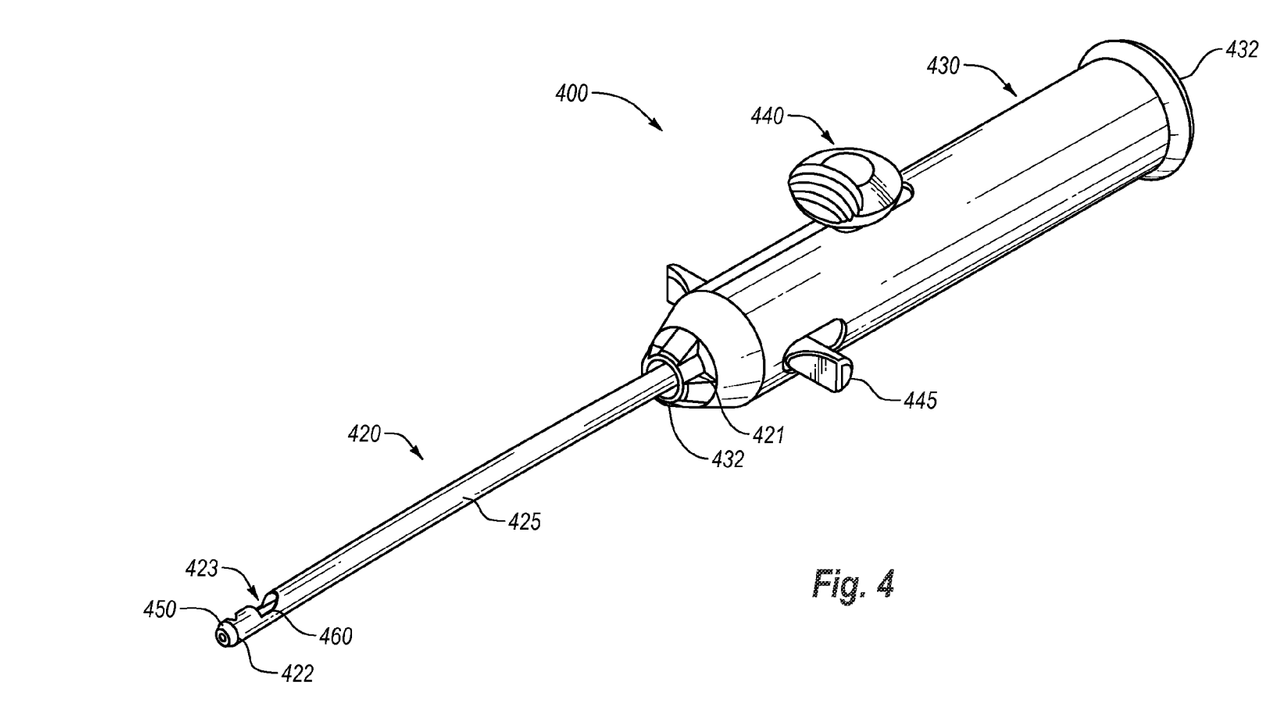
FIG. 4 discloses a suture trimmer in accordance with one example embodiment.

Referring now to FIG. 4, there is shown an exemplary embodiment of a suture trimmer 400. In accordance with the present disclosure, the suture trimmer 400 includes a shaft assembly 420 that that may be configured to deliver at least one hemostatic agent to the tissue surrounding an opening in a blood vessel without simultaneously introducing the at least one hemostatic agent into the patient's vasculature system.

As shown in FIG. 4, the suture trimmer 400 includes a shaft assembly 420. The shaft assembly 420 includes an elongated member 425 having a proximal end 421 and a distal end 422. An opening 423 is formed in the elongated member 425 adjacent to the distal end 422. A fitting 450 may be disposed adjacent to the distal end 422 of the shaft assembly 420. The fitting 450 may have a cross-sectional size no greater than that of the elongated member 425. The fitting 450 further includes a groove formed therein, wherein the groove is adapted to receive at least one length of suture therethrough. In a preferred embodiment, the groove is configured to receive at least two sutures therethrough. The distal face of the fitting 450 is configured to engage a knot formed in a suture loop, thereby enabling the suture trimmer 410 to be utilized as a knot pusher and advance the knot to an incision site. The face of the fitting may be formed having a convex, concave, or flat surface. Alternatively, the face may be formed at an angle relative to an axis extending through the shaft assembly.

The fitting 450 may be retained within the bore of the elongated member 425 through the use of mechanical fasteners or suitable adhesives. It is further contemplated that the fitting may be formed onto the elongated member utilizing a molding process. Alternatively, the fitting 450 and elongated member 425 may be integrally formed. The fitting 450 is preferably fabricated of a bio-compatible material, such as metal or plastic.

The shaft assembly 420 further comprises a cutting member 460 and a suture retaining member 428 disposed within the bore of the elongated member. The cutting member 460 and the suture retaining member 428 may be retained within the bore of the elongated member 425 coaxially, though it is contemplated that they may be retained in other manners, such as, side-by-side or offset. Both the cutting member 460 and the suture retaining member 428 are disposed for movement within the bore of the elongated member. In various embodiments, cutting member 460 is slidably or rotatably disposed within elongated member (i.e. shaft) 425, and suture retaining member 428 is either slidably or rotatable disposed within elongated member (i.e. shaft) 425. Preferably, the handle of the device includes two levers with the first lever being operatively coupled to the suture retainer and the second lever being operatively coupled to the cutting member.

Any portion of the shaft assembly 420 may include a hemostatic agent as a component of a coating on the shaft assembly 420. Suitable examples of hemostatic agents that can be included as a component of a coating on the shaft assembly 420 include, but are not limited to, aminocaproic acid, prothrombin, thrombin, thromboxane A2, thromboxane B2, endothelins, vasoconstrictors, adrenergic agents, angiotensins, lysine, polylysine, tranexamic acid, N-acetyl-lysine-methyl ester, bentonite, collagen, chitosan, cationic polymers, viscosity increasing polymers, anti-fibrinolytic proteins, coagulation catalyzing compounds, coagulation factors, or crosslinkers, derivatives thereof, pharmaceutically acceptable salts thereof, and combinations thereof.

In operation, closure of an opening in a vessel may be facilitated using the suture trimmer 400 by at least partially advancing the suture trimmer 400 into the tissue surrounding the opening. In particular, the operator may advance the suture trimmer 400 until the suture trimmer 400 contacts a suture loop that has been formed in the opening in the body lumen. For example, a suture loop includes a knot formed in a loop of suture, wherein the two free ends of the suture extend from the knot. The suture trimmer 400 may be used to tighten and trim the suture by capturing the suture by drawing the knot tight and cutting the free ends of the suture. Additional discussion of suture trimmers can be found in U.S. Pat. No. 7,094,246, the entirety of which is incorporated by reference in its entirety.

Notably, the shaft assembly 420 does not contact the inside of the body lumen during the process of tightening and trimming the suture. As such, the suture trimmer 400 described herein may be used to deliver a hemostatic composition to the tissue surrounding an opening in a body lumen while applying a closure element to the opening in the body lumen.

III. Methods for Administering a Hemostatic Agent

In one embodiment, the present disclosure may include a method for administering at least one hemostatic agent to a bodily tissue surrounding an opening formed in a body lumen. The method may include steps of (1) providing at least one elongate, substantially cylindrical element having an open proximal end, an open distal end, and a lumen extending therebetween and at least one hemostatic agent disposed on at least one region of the one elongate, substantially cylindrical element, and (2) inserting the elongate, substantially cylindrical element into a tissue surrounding a venous or arterial puncture site for performing a medical procedure so as to gain access to the venous or arterial puncture site and deliver the at least one hemostatic agent to the tissue surrounding the a venous or arterial puncture site while substantially not delivering the at least one hemostatic agent to the inside of the vein or artery.

Figure 5:
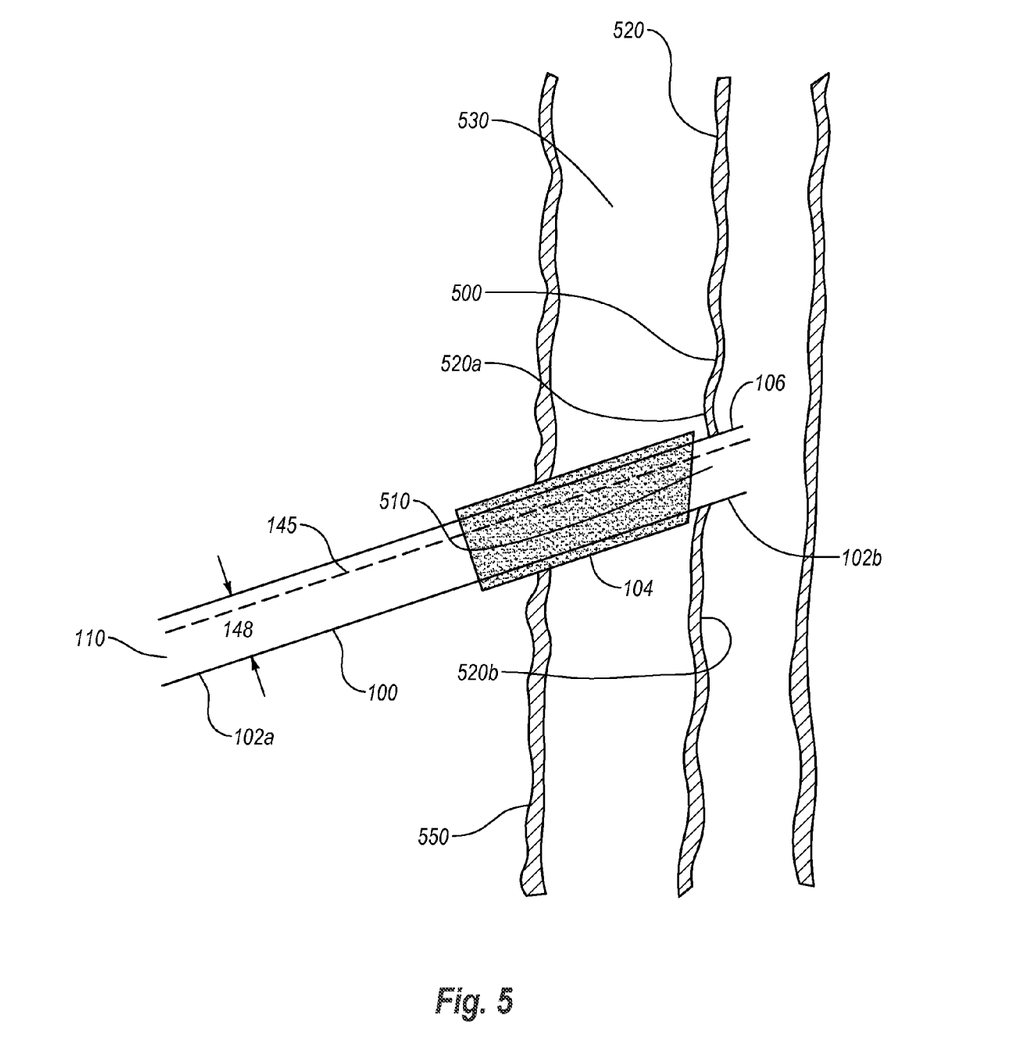
FIG. 5 illustrates a procedural sheath that is positioned through tissue and into an opening formed in a wall of a body lumen, according to one embodiment of the disclosure.

FIG. 5 illustrates a procedural sheath 100 that is positioned through tissue 530 and into an opening 510 formed in a wall 520 of a body lumen 500. The sheath 100 includes tissue contacting region 104, which includes one or more hemostatic agents, and a body lumen penetrating region that is devoid of hemostatic agent. The sheath 100 includes a proximal end 102a and a distal end 102b and an internal lumen 110 that can be used to introduce a number of devices into the body lumen 500.

Since the internal cross-section 148 of the sheath 100 may be less than or substantially equal to the cross section of the instruments inserted into the lumen 110, the sheath 100 may be configured to radially expand, such as by stretching. Alternatively, or in addition, the sheath 100 can be advantageously configured to split, thereby permitting the introduction of instruments larger than the lumen 110 into the body lumen 500. To facilitate the splitting, the sheath 100 can include one or more splits 145, such as longitudinal splits, each split being provided in the manner known in the art.

The sheath 100 may be inserted or otherwise positioned through skin 550 and tissue 530 and within a body lumen 500 (e.g., a blood vessel) via the opening 510. Region 104 is shown as an example of a portion of the sheath 100 that can be used to introduce one or more hemostatic agents to the non-vascular tissues (e.g., 530 and 550) surrounding the opening 510 while simultaneously not introducing the hemostatic agent beyond the wall 520 of the punctured lumen 500. While the tissue contacting region 104 will vary somewhat from situation to situation, the tissue contacting region 104 can be roughly defined as the portion of the sheath 100 that can contact the tissue 530 between the skin 550 and the outer surface of the body lumen 520a. As schematically illustrated by the shaded area in FIG. 5, the sheath 100 may include shading or other depth indicia on the tissue contacting region 104 to assist a practitioner in administering the hemostatic agent to the tissue surrounding the opening 530 while avoiding delivery of the hemostatic agent into the body lumen 500.

In one embodiment, the sheath 100 may be introduced into the opening 510 in the body lumen 500 by advancing the sheath 100 over a guide wire or other rail (not shown) which has been positioned through the opening 510 and into the body lumen 500 using conventional procedures. The sheath 100 is advanced so that the body lumen-penetrating region 106 enters into the body lumen 500 without the tissue-contacting region 104 entering the body lumen 500. As such, the hemostatic agent that is disposed at the tissue-contacting region 104 does not enter into the body lumen 500 such that the hemostatic agent does not contact any of the tissue on or around the inner wall 520b of the body lumen 500.

In one embodiment, the body lumen 500 may be a peripheral blood vessel, such as a femoral or carotid artery, although other body lumens may be accessed using the sheath 100 as will be appreciated by those skilled in the art. The opening 510, and consequently the sheath 100, may be oriented with respect to the blood vessel 500 such as to facilitate the introduction of devices through the lumen 110 of the sheath 100 and into the blood vessel 500 with minimal risk of damage to the blood vessel 500. One or more devices (not shown), such as a catheter, a guide wire, or the like, may be inserted through the sheath 100 and advanced to a preselected location within the patient's body. For example, the devices may be used to perform a therapeutic or diagnostic procedure, such as angioplasty, atherectomy, stent implantation, and the like, within the patent's vasculature. In addition to being usable with the apparatuses described herein, suture devices, clip appliers, plug appliers, and the like typically include elongate members that can be used to deliver at least one hemostatic agent to the tissue surrounding an opening consistent with the description of the apparatuses and methods described herein.

For example, U.S. Pat. No. 5,304,184, issued to Hathaway et al. describes a device for percutaneously suturing a puncture site. U.S. Pat. No. 5,674,231, issued to Green et al., discloses a deployable loop that may be advanced through a sheath into a vessel. The loop is intended to resiliently expand to engage the wall of the vessel, thereby closing the puncture. U.S. Pat. No. 6,197,042 and pending U.S. patent application Ser. No. 10/638,115 filed Aug. 8, 2003 entitled "Clip Applier and Methods" describe apparatuses that can be used to deliver a clip device that can be used to close a puncture in a blood vessel or another body lumen. In another example, U.S. Pat. Nos. 5,192,302 and 5,222,974, issued to Kensey et al., describe the use of a biodegradable plug that may be delivered through an introducer sheath into a puncture site. Each of the above referenced patents and applications describe devices that can be used with the sheath devices described herein. Each of the above described devices also include elongate members that can be used to deliver at least one hemostatic agent to the tissue surrounding an opening consistent with the description of the apparatuses and methods described herein. Each of the above described patent and applications are incorporated herein by reference in their entireties.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

We claim:

1. A method for administering at least one hemostatic agent to a bodily tissue surrounding an opening in a body lumen, the method comprising:
   providing at least one elongate element having an open proximal end, an open distal end, and a lumen extending therebetween and the at least one elongate element having a tissue contacting region coated with a hemostatic agent thereon, the elongate element including depth indicia configured to designate the tissue-contacting region, wherein the depth indicia are selected from the group consisting of a first color on the tissue-contacting region and a second color on an optional body lumen-penetrating region, at least a first bleed back lumen positioned distal to the tissue contacting region, and combinations thereof; and
   facilitating stoppage of bleeding from the opening in the body lumen by inserting the elongate element into the tissue surrounding the opening in the body lumen and applying the at least one hemostatic agent onto the tissue surrounding the opening in the body lumen by contacting the tissue surrounding the opening in the body lumen with at least a portion of the tissue contacting region, while substantially not delivering the at least one hemostatic agent to the inside of the vein or artery.

2. The method recited in claim 1, the at least one hemostatic agent being selected from a group consisting of aminocaproic acid, prothrombin, thrombin, thromboxane A2, thromboxane B2, an endothelin, a vasoconstrictor, an adrenergic agent, an angiotensin, lysine, polylysine, tranexamic acid, N-acetyl-lysine-methyl ester, bentonite, collagen, chitosan, cationic polymers, viscosity increasing polymers, anti-fibrinolytic proteins, coagulation catalyzing compounds, coagulation factors, or crosslinkers, derivatives thereof, pharmaceutically acceptable salts thereof, and combinations thereof.

3. The method recited in claim 1, wherein the elongate element is an introducer sheath configured to allow access to the body lumen during a medical procedure.

4. The method recited in claim 1, wherein the elongate element includes a closure element delivery device configured to deliver a closure element to the wall of the body lumen, and wherein the closure element delivery device includes a tube set capable of contacting the tissue surrounding the opening.

5. The method recited in claim 1, wherein the elongate element includes a suture trimmer configured for tightening and trimming a suture applied to the wall of the body lumen, and wherein the suture trimmer includes a tube set capable of contacting the tissue surrounding the opening.

6. The method recited in claim 1, further comprising using the depth indicia to insert the elongate element into the tissue surrounding the opening in the body lumen so as to deliver the at least one hemostatic agent to the tissue surrounding the venous or arterial puncture site while substantially not delivering the at least one hemostatic agent to the inside of the vein or artery.

7. The method of claim 1, further comprising radially expanding the elongate member.

8. The method of claim 1, further comprising introducing a device through the lumen of the elongate member into the body lumen.

9. The method of claim 8, wherein the device introduced through the lumen of the elongate member into the body lumen is selected from the group consisting of a catheter and a guide wire.

10. The method of claim 1, further comprising applying a clip or a plug to or into the tissue surrounding the opening in the body lumen.

11. A method for administering at least one hemostatic agent to a bodily tissue surrounding an opening in a body lumen, the method comprising:
   inserting a tissue contacting region of an elongate element into the tissue surrounding the opening in the body lumen, the tissue contacting region of the elongated element being coated with a hemostatic agent, the elongate element including depth indicia configured to designate the tissue-contacting region, wherein the depth indicia are selected from the group consisting of a first color on the tissue-contacting region and a second color on an optional body lumen-penetrating region, at least a first bleed back lumen positioned distal to the tissue contacting region, and combinations thereof;
   positioning the elongate element relative to the tissue surrounding the opening in the body lumen by deploying an anchor member within the body lumen;

contacting the tissue surrounding the opening in the body lumen with at least a portion of the tissue contacting region;

facilitating stoppage of bleeding from the opening in the body lumen by applying the hemostatic agent to the tissue surrounding the opening in the body lumen; and retracting the anchor member from the body lumen after applying the hemostatic agent to the tissue surrounding the opening in the body lumen.

12. The method of claim 11, further comprising expanding the anchor member from an initial contracted configuration to a deployed expanded configuration.

13. The method of claim 12, further comprising contracting the anchor member.

14. The method of claim 11, wherein the anchor member is deployed from a lumen extending between the distal end and the proximal end of the elongate element.

15. The method of claim 11, wherein the anchor member is further retracted into the lumen of the elongate element.

16. The method of claim 11, further comprising applying a clip or a plug to or into the tissue surrounding the opening in the body lumen.

\* \* \* \* \*